United States Patent [19]

Azer et al.

[11] Patent Number: 5,003,969
[45] Date of Patent: Apr. 2, 1991

[54] FRACTURE ALIGNMENT DEVICE

[75] Inventors: Samir N. Azer, Alexandria, Va.; Naser N. Salman, Rockville, Md.; William R. Krause, Richmond, Va.

[73] Assignee: Orthopedic Designs, Inc., Alexandria, Va.

[21] Appl. No.: 482,805

[22] Filed: Feb. 21, 1990

[51] Int. Cl.$^5$ ............................................. A61F 5/04
[52] U.S. Cl. .................................. 128/87 R; 606/54; 128/84 C
[58] Field of Search ............... 128/87 R, 84 B, 84 C, 128/90, 165, 878, 879; 606/53–59

[56] References Cited

U.S. PATENT DOCUMENTS 3,299,888  1/1967  Muckinhaupt ..................... 128/87 R
4,584,995  4/1986  Koeneman ............................ 606/54

Primary Examiner—Robert A. Hafer
Assistant Examiner—Michael Brown
Attorney, Agent, or Firm—Fleit, Jacobson, Cohn, Price, Holman & Stern

[57] ABSTRACT

A fracture alignment and retention device includes a plurality of spanning bars which are spaced about the extremity of the patient having a fractured long bone. Preferably, the spanning bars are located circumferentially about the extremity. At least three spanning bars are held in approximately 90 degree offset positions with respect to each other by two straps encircling the extremity. The straps are secured in place by a VELCRO-type fastener or other securing devices. Each spanning bar includes at least two pressure pads which are placed on the extremity on opposite sides of the fracture. Each pressure pad includes a threaded shaft which is threadably mounted at a central portion in a fixed bushing engaged in a slot defined in an uppermost surface of the spanning bar. One end of the shaft includes a knob and the opposite end is mounted on the pressure pad for causing movement of the pressure pad toward or away from the extremity in an axial direction along the shaft without rotation of the pressure pad. Rotation of knobs located at the end of the shaft controls the amount of pressure exerted against the extremity by the pressure pads and includes an indicator for noting relative positioning of a knob prior to and after turning of the knob.

14 Claims, 2 Drawing Sheets

FRACTURE ALIGNMENT DEVICE

FIELD OF THE INVENTION

This invention relates to a device for alignment of fragments of a fractured long bone in a sterile surgical environment so as to obtain proper alignment of the bone fragments.

BACKGROUND OF THE INVENTION

It is imperative that fractures of long bones be properly aligned prior to fixation by an intramedullary nail, for example. Improperly aligned bone fragments may result in difficulty in insertion of a fixation device. Since it is imperative to obtain bone alignment of the fracture fragments prior to fixation, crude methods are currently used to obtain such alignment.

Present practices for alignment of fractured long bone fragments include mechanisms for holding a patient's extremity in a fixed position. Such mechanisms include the se of rigid boards, leverage devices or rings around the extremity as a gross relative adjustment of the bone fragments. For precise alignment of the bone fragments, the hands of a surgeon are often subject to continuous exposure of the x-rays from a fluoroscopic image intensifier as the bone fragments are realigned in all planes. The final alignment of the bone fragments is achieved by shifting of the extremity of the patient during constant fluoroscopic radiation exposure to the hands of the surgeon over an extended length of time as the hands of the surgeon hold the bone fragments in position. Once the bone fragments are aligned, an intramedullary fixation procedure may be, used to secure the bone fragments in an aligned position.

SUMMARY OF THE INVENTION

It is therefore an object of the present invention to overcome the disadvantages of prior systems for alignment of bone fragments.

By the present invention, a fracture alignment and retention device includes a plurality of spanning bars which are spaced about the extremity of the patient having a fractured long bone. Preferably, the spanning bars are located circumferentially about the extremity.

The spanning bars are placed at any point around the circumference of the extremity to correspond to the prominent ends of the fracture fragments. The straps may be held in approximately 90 degree offset positions with respect to each other by two straps encircling the leg. The straps are secured in place by a VELCRO-type fastener or other securing means. Each spanning bar includes two pressure pads which are placed on the extremity on opposite sides of the fracture. Each pressure pad includes a threaded shaft which is threadably mounted at a central portion in a fixed bushing engaged in a slot defined in an uppermost surface of the spanning bar. One end of the shaft includes a knob and the opposite end is mounted on the pressure pad for causing movement of the pressure pad toward or away from the extremity in an axial direction along the shaft without rotation of the pressure pad. Rotation of the knob located at the end of the shaft controls the amount of pressure exerted against the extremity by the pressure pads and includes an indicator for noting relative positioning of a knob prior to and after turing of the knob.

Two bone fragments are aligned relative to each other by applying pressure via he pressure pads to the extremity so as to shift the bone fragments into alignment in all planes. The spanning bars, straps, handles, shafts, and bushings are made of a radio-transparent material so that when the retention device is viewed under a fluoroscope with the hands of the surgeon removed from the field of view, the retention device will not obstruct the viewing field. Radio-opaque identifiers such as wires are embedded in the pressure pads along its periphery so as to provide a position indicator of the pressure pads when viewing the bone fragments with the fluoroscope. By adjustment of the pressure pads aligned in different planes about the extremity, the bone fragments are shifted into alignment for a subsequent insertion of an internal fixation device such as an intramedullary nail.

It is therefore another object of the present invention to provide a fracture alignment device having spanning bars in spaced planes for aligning fragments of a fractured long bone.

It is yet another object of the present invention to provide a fracture alignment device having spanning bars in spaced planes for aligning fragments of a fractured long bone with each spanning bar including at least two pressure pads located on circumferential point of the fracture for aligning the bone fragments.

It is still et another object of the present invention to provide a fracture alignment device having spanning bars in spaced planes for aligning fragments of a fractured long bone with each spanning bar including at least two pressure pads located on circumferential point of the fracture for aligning the bone fragments with pressure pads including a radio-opaque material for viewing under a fluoroscope the relative positions of the pressure pads with respect to the bone fragment.

It is still yet another object of the present invention to provide a fracture alignment device having spanning bars in spaced planes for aligning fragments of a fractured long bone with each spanning bar including at least two pressure pads located on circumferential points of the fracture for aligning the bone fragments with the pressure pads including a radio-opaque material for viewing under a fluoroscope the relative positions of the pressure pads with respect to the bone fragments with pressure pads being adjustable in position to move towards and away from the extremity of the patient.

These and other objects of the invention, as well as many of the intended advantages thereof, will become more readily apparent when reference is made to the following description taken in conjunction with the accompanying drawings.

DETAILED DESCRIPTION OF THE PREFERRED EMBODIMENTS

Figure 1:
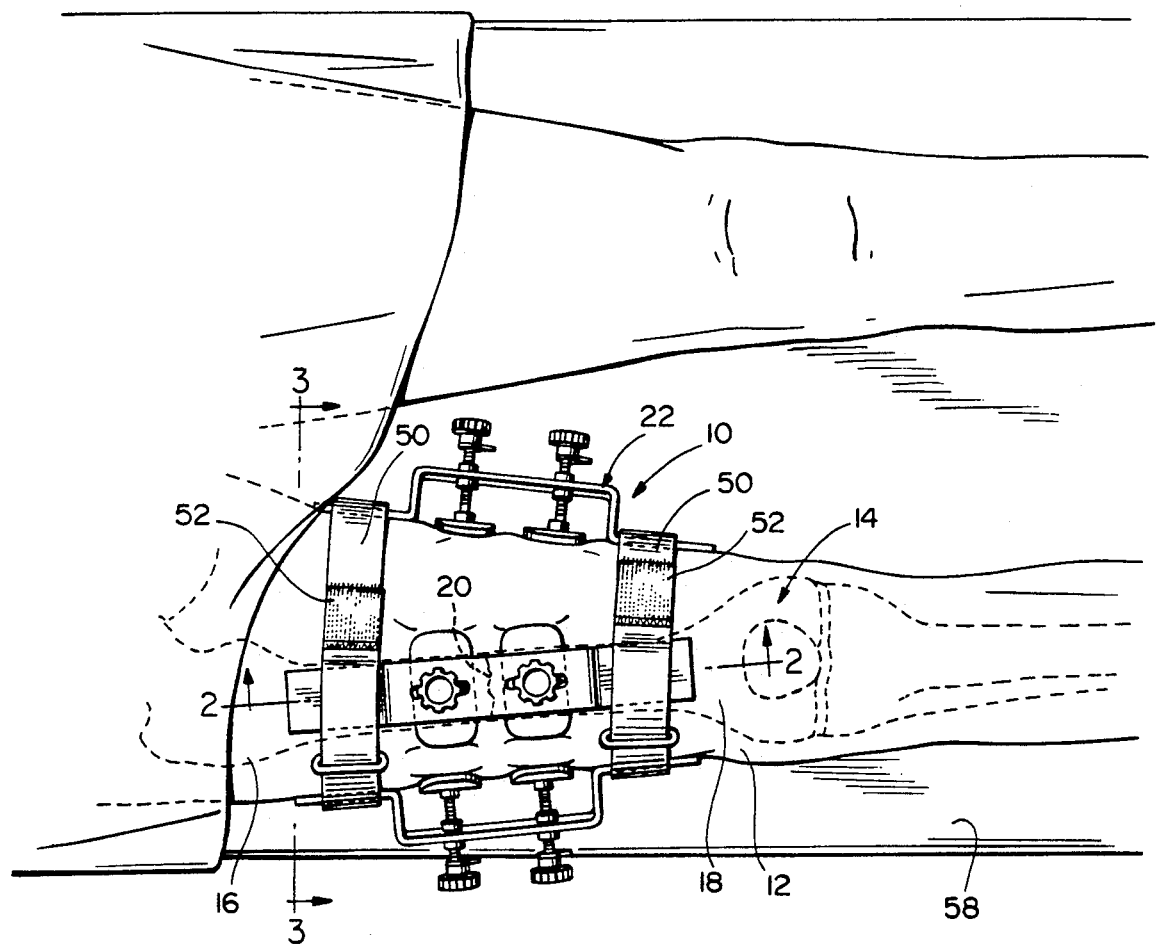
FIG. 1 is a top plan view of a patient on a fracture table having the retention device of the present invention secured about a fractured femur.

In describing a preferred embodiment of the invention illustrated in the drawings, specific terminology will be resorted to for the sake of clarity, however, the invention is not intended to be limited to the specific terms so selected, and it is to be understood that each specific term includes all technical equivalents which operate in a similar manner to accomplish a similar purpose.

Figure 2:
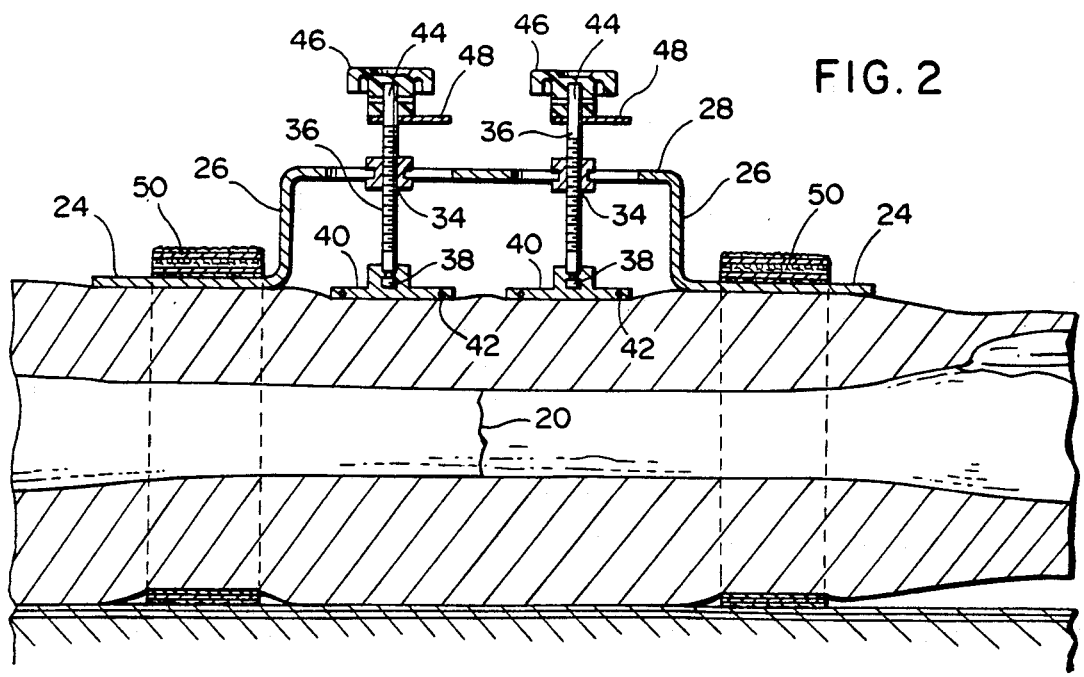
FIG. 2 is longitudinal section taken along line 2—2 of FIG. 1.
Figure 3:
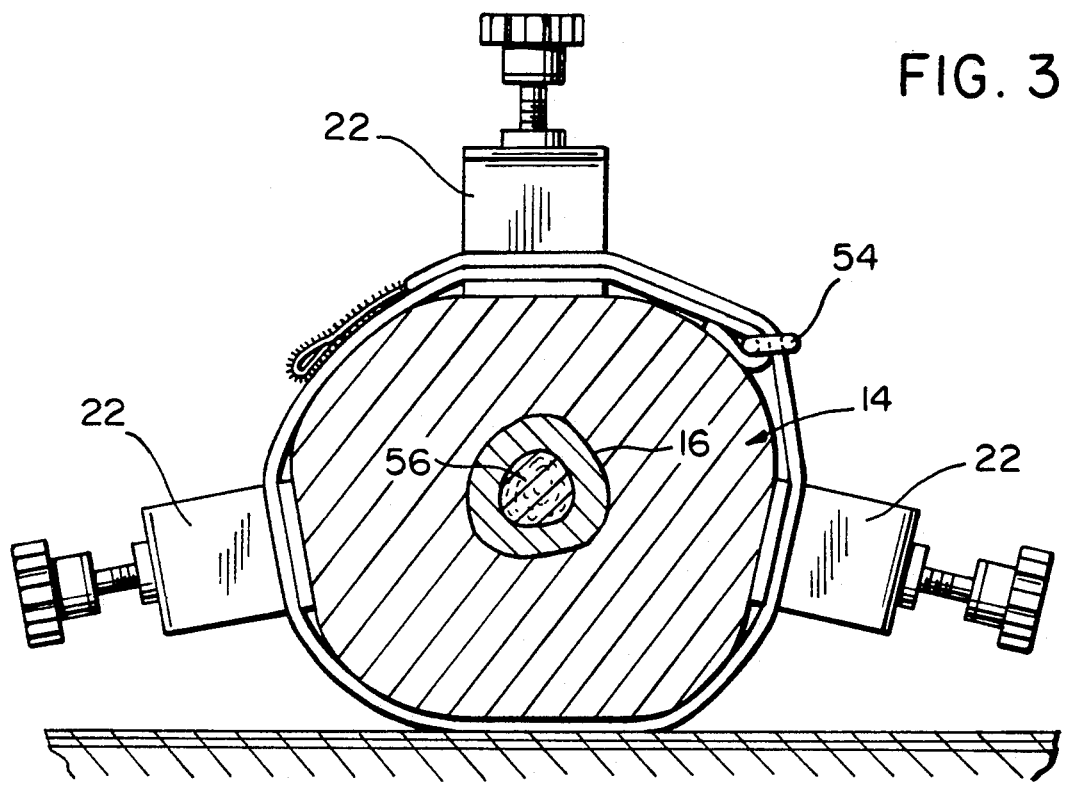
FIG. 3 is a cross-section as viewed along line 3—3 of FIG. 1.

With reference to the drawings, in general, and to FIGS. 1 to 3, in particular, a fracture alignment and retention device embodying the teachings of the subject invention is shown and a method of its use is described with the fracture alignment and retention device being generally designated as 10. With reference to its orientation in FIG. 1, the fracture alignment and retention device is located about a leg 12 of a patient having a fractured femur 14 with bone fragments 16 and 18 located on opposite sides of fracture line 20.

Figure 4:
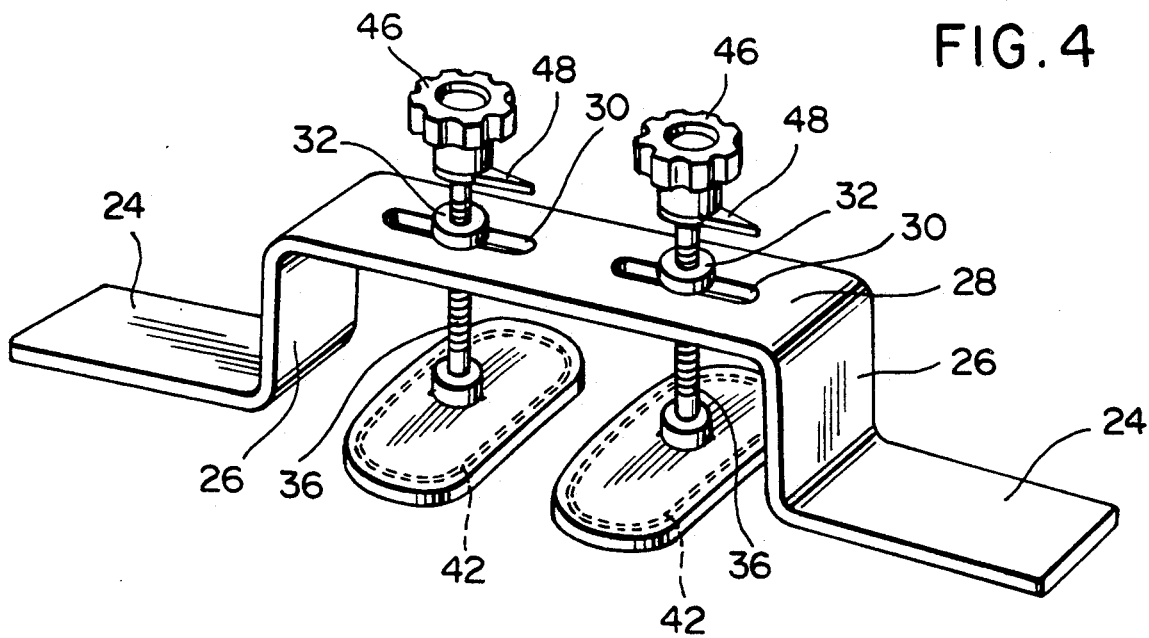
FIG. 4 is a perspective view of a spanning bar having two adjustable pressure pads.

Fracture alignment and retention device 10 comprises a plurality of spanning bars 22, which, as shown in FIGS. 2 and 4, include two terminal end portions 24 for resting against the leg 14 of the patient. Two riser portions 26 interconnect the end portions 24 and a raised section 28. Section 28 includes, as shown in FIG. 4, two longitudinally extending slots 30 within which are fixed a slidable bushing 32 having an internally threaded bore 34 for receipt of a threaded shaft 36. One end 38 of the threaded shaft 36 is mounted in a pressure pad 40 for rotation of the shaft without rotation of the pressure pad. The threads of the shaft 36 engage threaded bore 34 so as to move the pressure pad in a direction parallel to the axis of the shaft 36 and towards or away from the leg of the patient. The pressure pads are positioned with respect to the fracture line by the sliding of bushing 32 in slot 30.

Pressure pad 40 includes a radio-opaque wire 42 as shown in phantom lines in FIGS. 1 and 4, and shown in solid lines in FIG. 2. Wire 42 extends about the periphery of the pressure pad and is embedded in the pad. The longitudinal axis of the pressure pad extends perpendicular to the longitudinal axis of the spanning bar. At an opposite end 44 of threaded shaft 36 is mounted a turning knob 46, having an indicator 48 fixed to the handle, for indicating relative amount of movement of th knob after turning of the knob for displacement of the pressure pad 42 axially along the longitudinal axis of the threaded shaft 36.

The three spanning bars shown in FIGS. 1 and 3 are held in position about the fractured femur by straps 50 having VELCRO-type fastening sections 52 for securing the strap onto itself after being threaded through a loop 54 and reversing direction of the strap to be secured onto itself. The strap is sufficiently tightened to secure the portions 24 of the spanning bars in place on the leg of the patient. The spaning bars are sufficiently rigid to force the pressure pads against the leg of the patient during clockwise rotation of the shafts 36. The spanning bar may be made of graphite and epoxy for strength and radio-transparent radiographic viewing through the spanning bars so as to prevent masking of adjustments of the pressure pads when viewed under a fluoroscope.

For alignment of the fractured bone segments 16 and 18, so that an intramedullary nail may be placed through the central marrow core 56 of the femur, the field of the fracture is viewed by the surgeon with the hands of the surgeon removed from the field of view so as to locate the relative positioning of the bone fragments. By quickly moving the surgeon's hand into the field of view and rotating the knobs 46 on opposite sides of the fracture line 20 and in different planes of the leg and then removing the surgeon's hands from the field of view, pressure is applied to the leg by the pressure pads so as to move the bone fragments toward each other for alignment in all planes. Once an adjustment is made, the bone fragments remain fixed in position by the pressure from the pressure pads.

By movement of the bushings 32 within slots 30, the threaded shafts 36 and their attached pressure pads may be moved towards or away from each other in different planes or moved in a single direction in unison for proper alignment of the bone fragments on opposite sides of the fracture line 20. Additionally, four spanning bars may be used spaced circumferentially about the leg of the patient which is supported in free suspension by the fracture table 58.

The fracture segments 16 and 18 are aligned by a continuous process of tightening or releasing of pressure by the various pressure pads by rotation of knobs 46 based on the images presented by a fluoroscope image intensifier without the surgeon's hands being in the field of view. This method prevents excessive exposure to x-rays by the surgeon, and especially to the surgeon's hands, during the alignment of the bone fragments.

Having described the invention, many modifications thereto will become apparent to those skilled in the art to which it pertains without deviation from the spirit of the invention as defined by the scope of the appended claims.

We claim:

1. A fracture alignment and retention device comprising:
    alignment means for aligning bone fragments,
    said alignment means including elongated members spaced about the periphery of an extremity of a patient and being substantially radio-transparent,
    said alignment means mounted on said elongated members including pressure means for shifting bone fragments with respect to each other in different planes of the bone fragments so as to align the bone fragments along a longitudinal axis, and
    said pressure means including radio-opaque means for viewing a location of said pressure means under a fluoroscope and means for securing said elongated member to extremity of the patient.

2. A fracture alignment and retention device as claimed in claim 1, wherein said alignment means includes a plurality of spanning bars located along the extremity of the patient and extending across a fracture between the bone fragments.

3. A fracture alignment and retention device as claimed in claim 2, wherein said pressure means includes at least two pressure pads movably mounted with respect to each of said spanning bars.

4. A fracture alignment and retention device as claimed in claim 3, wherein said at least two pressure pads are slidably mounted with respect to each of said spanning bars.

5. A fracture alignment and retention device as claimed in claim 3, wherein said at least two pressure pads are mounted at one end of threaded shafts, said threaded shafts extending through a threaded member mounted on said spanning bar and said threaded shafts terminating in a knob rotatable for movement of said pressure pad toward or away from said threaded member upon rotation of said handle.

6. A fracture alignment and retention device as claimed in claim 2, wherein said pressure means are mounted on said spanning bars.

7. A fracture alignment and retention device as claimed in claim 6, wherein said spanning bars are positioned circumferentially about the extremity.

8. A fracture alignment and retention device as claimed in claim 3, wherein said at least two pressure pads are mounted on opposite sides of the fracture between the bone fragments.

9. A fracture alignment and retention device comprising:
elongated spanning bars for placement about an extremity of a patient having bone fragments located on opposite sides of a fracture line, said bars adapted to extend along the extremity of the patient in different planes so as to have opposite ends located on opposite sides of the fracture line, said bars being radio-transparent,
pressure pad means movably mounted on each of said bars for shifting bone fragments with respect to each other, said pressure pad means being radio-transparent,
radio-opaque means mounted on said pressure pad means for viewing the location of said pressure pad means under a fluoroscope, and
mounting means for mounting said bars on the extremity of the patient.

10. A fracture alignment and retention device as claimed in claim 9, wherein said pressure pad means includes a threaded shaft mounted in a threaded bushing, said threaded bushing being mounted on each of said bars.

11. A fracture alignment and retention device as claimed in claim 10, wherein said bushing is slidably mounted in a slot of each of said bars.

12. A fracture alignment and retention device as claimed in claim 11, wherein said pressure pad means includes a pressure pad mounted at one end of said shaft.

13. A fracture alignment and retention device as claimed in claim 12, wherein said radio-opaque means is embedded in said pressure pad.

14. A fracture alignment and retention device as claimed in claim 9, wherein said mounting means is radio-transparent.

* * * * *